(12) United States Patent
Piantoni et al.

(10) Patent No.: US 9,968,491 B2
(45) Date of Patent: May 15, 2018

(54) MACHINE FOR MAKING ABSORBENT SANITARY ARTICLES

(71) Applicant: GDM S.p.A., Bologna (IT)

(72) Inventors: Matteo Piantoni, Albino (IT); Alberto Perego, Milan (IT)

(73) Assignee: GDM S.P.A., Bologna (IT)

(*) Notice: Subject to any disclaimer, the term of this patent is extended or adjusted under 35 U.S.C. 154(b) by 272 days.

(21) Appl. No.: 14/440,290

(22) PCT Filed: Nov. 21, 2013

(86) PCT No.: PCT/IB2013/060311
§ 371 (c)(1),
(2) Date: May 1, 2015

(87) PCT Pub. No.: WO2014/087293
PCT Pub. Date: Jun. 12, 2014

(65) Prior Publication Data
US 2015/0297416 A1 Oct. 22, 2015

(30) Foreign Application Priority Data
Dec. 3, 2012 (IT) .............................. BO2012A0655

(51) Int. Cl.
*A61F 13/49* (2006.01)
*B32B 37/00* (2006.01)
(Continued)

(52) U.S. Cl.
CPC .. *A61F 13/15634* (2013.01); *A61F 13/15585* (2013.01); *A61F 13/15699* (2013.01);
(Continued)

(58) Field of Classification Search
None
See application file for complete search history.

(56) References Cited

U.S. PATENT DOCUMENTS 6,730,189 B1 * 5/2004 Franzmann ....... A61F 13/15756
156/265
8,790,232 B2 * 7/2014 Pastrello .......... A61F 13/15756
493/379
(Continued)

FOREIGN PATENT DOCUMENTS

EP 0812789 12/1997
EP 1062928 12/2000
(Continued)

OTHER PUBLICATIONS

International Search Report dated Feb. 28, 2014 for related PCT Application No. PCT/IB2013/060311.

*Primary Examiner* — Linda L Gray
(74) *Attorney, Agent, or Firm* — Shuttleworth & Ingersoll, PLC; Timothy J. Klima

(57) ABSTRACT

A machine for making absorbent sanitary articles includes a device for feeding a continuous strip to a conveyor roller and to a device for cutting the strip into first and second pieces. A unit forms and applies at least a pair of first and second pieces, aligned and spaced by a distance (d), for each absorbent article A first and a second roller each comprising a plurality of units pick up and successively release of first and the second pieces. A plurality of concentric units rotating, independently of each other, about a shared axis of rotation, each carries at least one unit. A motor defines a respective law of motion for each of the units and a mechanism translates the units, between a position for picking up the pieces, at the conveyor roller, and a position for releasing the pieces, at the forming and applying unit.

16 Claims, 8 Drawing Sheets

(51) Int. Cl.
  *B32B 38/04* (2006.01)
  *A61F 13/15* (2006.01)
  *B65H 39/14* (2006.01)
  *B32B 38/00* (2006.01)

(52) U.S. Cl.
  CPC .. *A61F 13/15723* (2013.01); *A61F 13/15756* (2013.01); *A61F 13/15764* (2013.01); *A61F 13/15804* (2013.01); *B65H 39/14* (2013.01); *A61F 13/15577* (2013.01); *A61F 2013/15821* (2013.01); *B32B 37/0053* (2013.01); *B32B 38/0004* (2013.01); *B65H 2403/511* (2013.01); *B65H 2406/34525* (2013.01); *B65H 2801/57* (2013.01); *Y10T 156/1077* (2015.01); *Y10T 156/1087* (2015.01); *Y10T 156/1098* (2015.01); *Y10T 156/1322* (2015.01)

(56) References Cited

U.S. PATENT DOCUMENTS

| | | |
|---|---|---|
| 2003/0066609 A1 | 4/2003 | Calvert |
| 2008/0276439 A1 | 11/2008 | Andrews et al. |
| 2010/0192739 A1 | 8/2010 | Piantoni et al. |
| 2010/0326796 A1 | 12/2010 | Walsh |
| 2012/0190523 A1 | 7/2012 | Pastrello et al. |

FOREIGN PATENT DOCUMENTS

| | | |
|---|---|---|
| EP | 1303240 | 4/2003 |
| JP | 2002253606 A | 9/2002 |
| JP | 2007212307 A | 8/2007 |
| JP | 2009292618 A | 12/2009 |

\* cited by examiner

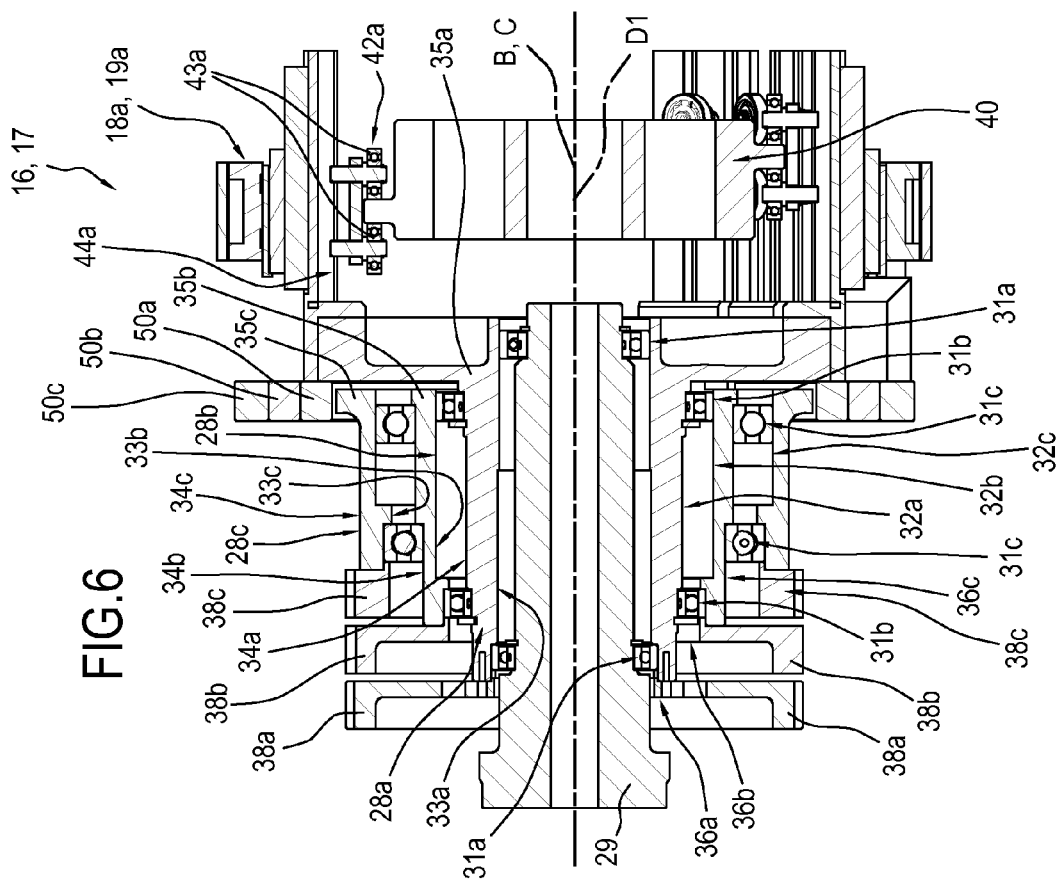
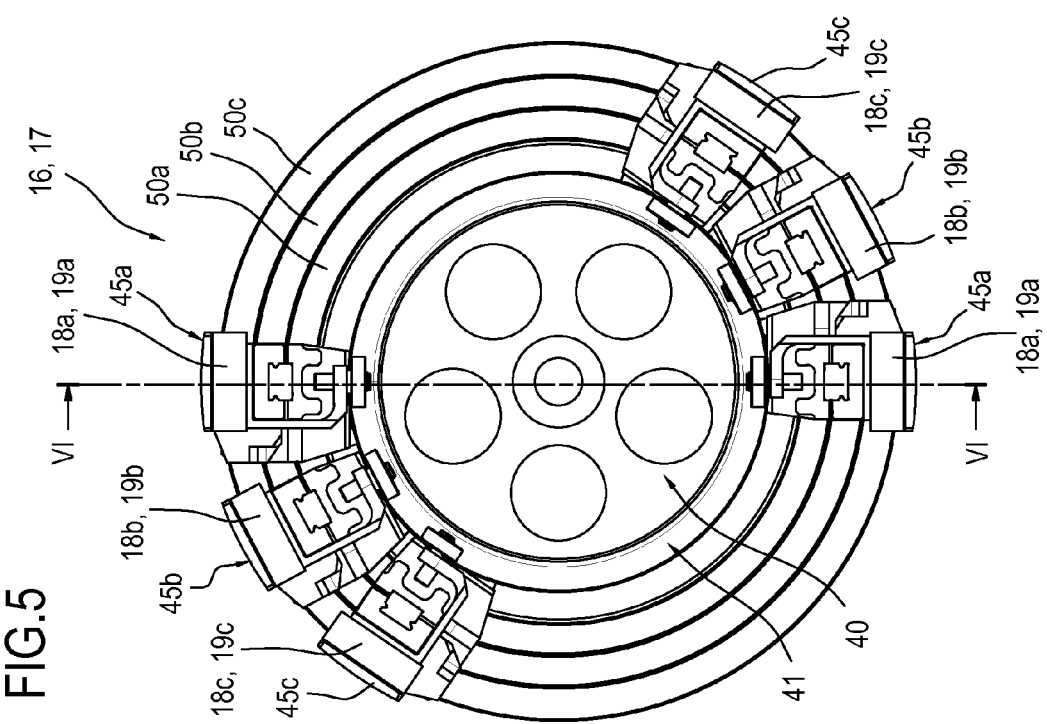

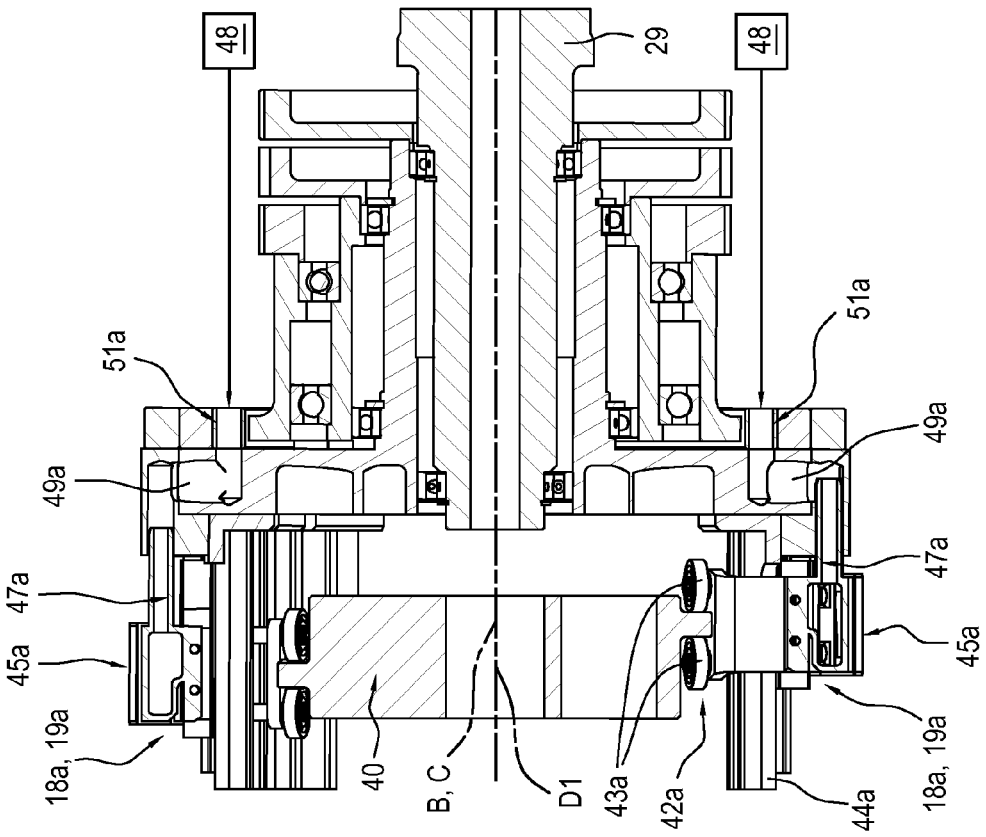
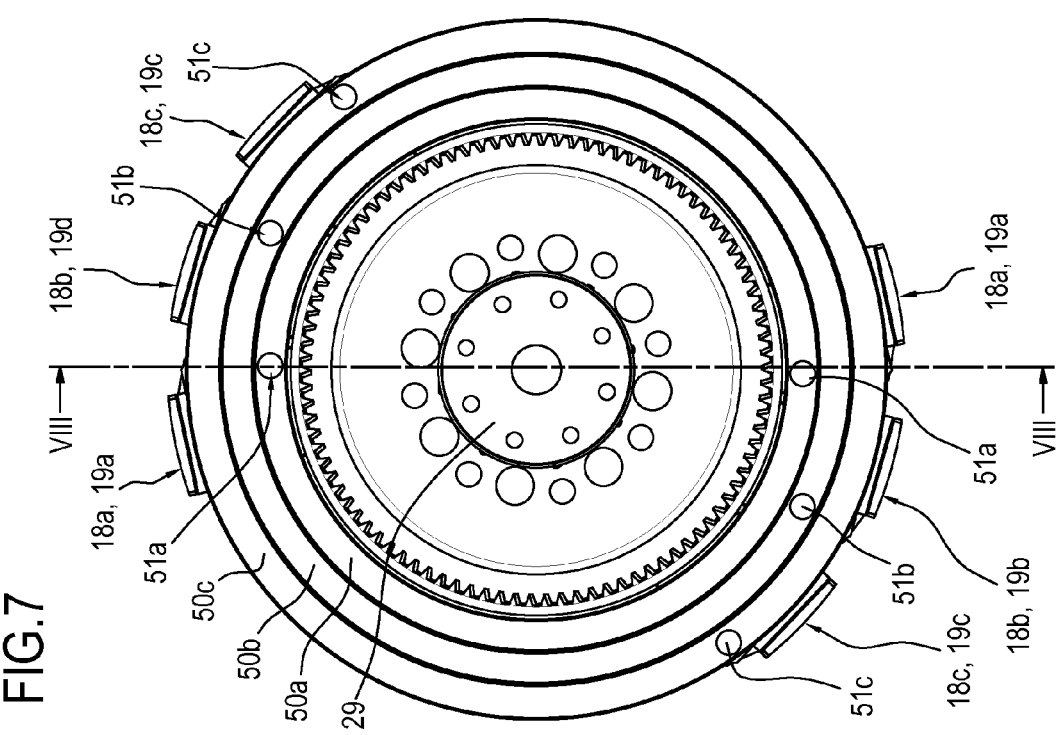

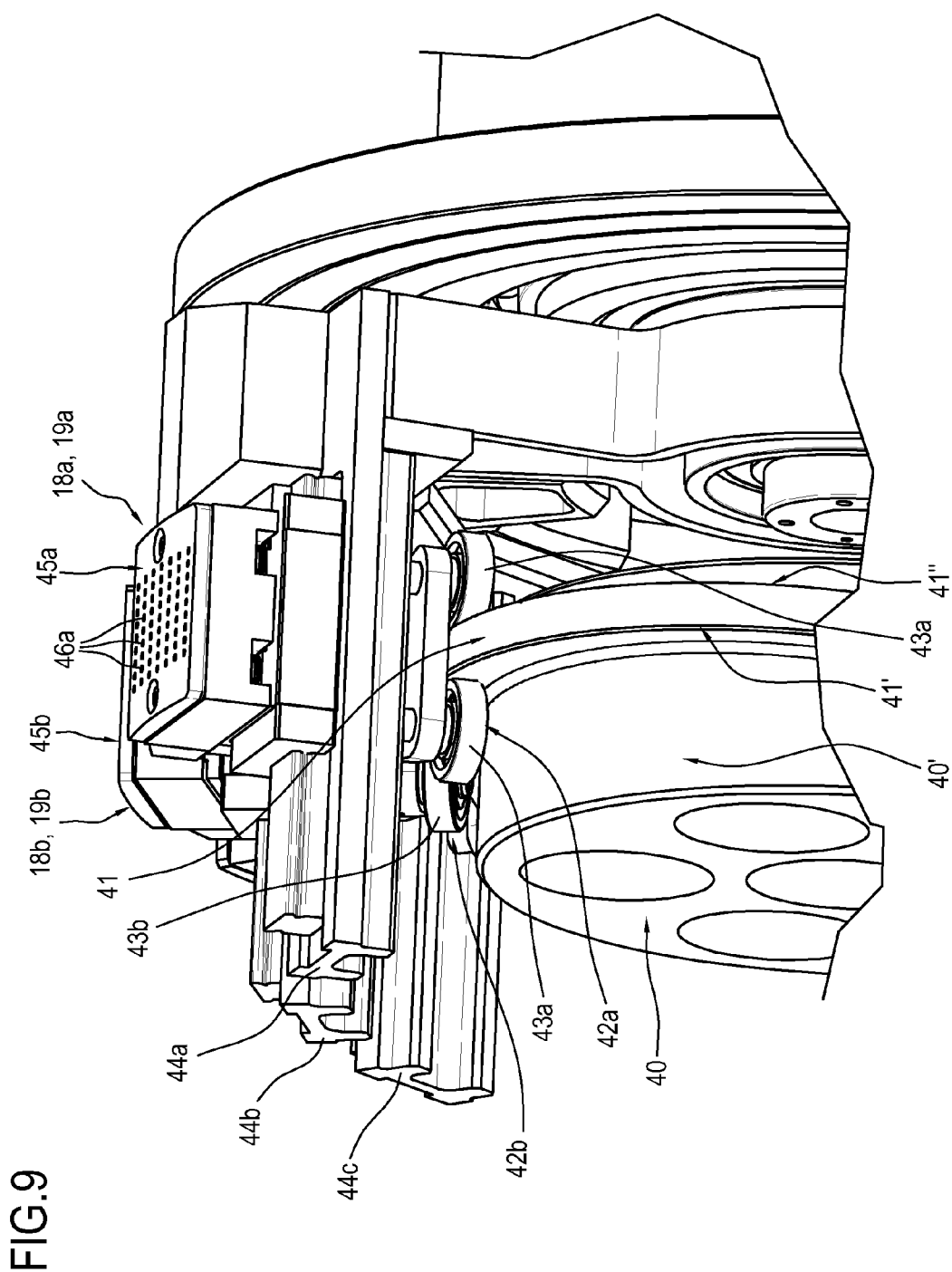

MACHINE FOR MAKING ABSORBENT SANITARY ARTICLES

This application is the National Phase of International Application PCT/IB2013/060311 filed Nov. 21, 2013 which designated the U.S. and that International Application was published under PCT Article 21(2) in English.

This application claims priority to Italian Patent Application No. BO2012A000655 filed Dec. 3, 2012, which application is incorporated by reference herein.

TECHNICAL FIELD

This invention relates to a machine for making absorbent sanitary articles.

More specifically, the invention relates to a machine for making absorbent sanitary articles such as disposable nappies for children or adults.

BACKGROUND ART

As is known, these articles are obtained by laying a sheet of impermeable material over a sheet of permeable material (of non-woven fabric), with a padding consisting of an absorbent pad interposed between the two sheets. More specifically, both in the case of nappies of children and in the case of nappies for adults, it is usual to add accessory components such as lateral flaps for closing the nappy round the wearer's waist.

Generally speaking, in the prior art machines, the lateral closure flaps are applied along certain stretches of a continuous web of a material for making nappies, these stretches corresponding to the single nappies, when subsequently divided.

These machines comprise a conveyor for feeding a continuous strip of elastomeric material, a device for cutting a continuous strip of elastomeric material into suitably shaped single pieces constituting the lateral flaps for closing the nappies, and a unit for forming and applying pairs of lateral flaps to the continuous band.

The cutting device makes a succession of pieces forming the above-mentioned lateral flaps which are fed by a conveyor roller to the unit for forming and applying the pairs of lateral flaps.

More in detail, each pair of lateral flaps is defined by a first and a second piece, and the cutting device makes a continuous and alternating succession of first and second pieces.

Between the conveyor roller and the forming and applying unit, the machine has a pair of spacer rollers, which are able to pick up respective pieces from the continuous succession fed by the conveyor roller.

A first spacer roller picks up from the succession only the first piece, whilst the second picks up only the second pieces.

The first and the second roller feed the respective pieces to the forming and applying unit, which makes the respective pairs of first and second pieces, which are mutually aligned and spaced by a predetermined length on the basis of the transversal dimensions of the continuous band of a material for making nappies. The forming and applying unit then applies in step each pair on the continuous band.

More specifically, it is known how, with the variation in the type of absorbent article to be made, the dimensions and the format of the lateral flaps also vary.

It is therefore necessary to replace one or more devices of the machine with others suitable to operate according to the new format of the absorbent article and the lateral flaps to be applied.

The new devices generally have new and different structural and functional characteristics and, therefore, problems occur linked to the operational or structural incompatibility between the new devices and those replaced.

To overcome this problem, further additional devices are used which act between the various devices replaced and those not replaced, resulting, however, in a further increase in the structural and functional complexity of the machine and the costs for making and preparing the machine for the new format to be made.

DISCLOSURE OF THE INVENTION

This invention has for an aim to provide a machine for making absorbent sanitary articles which overcomes the above mentioned disadvantages of the prior art.

In particular, the main aim of this invention is to provide a machine for making absorbent sanitary articles which is, overall, structurally simple and compact.

A further aim of this invention is to provide a machine for making absorbent sanitary articles which has a greater operational flexibility if the format of the article to be made is changed and which allows the number of devices present after a format change to be reduced.

These aims are fully achieved by a machine for making absorbent sanitary articles having features as disclosed herein.

Further advantageous aspects of the machine are set forth herein.

BRIEF DESCRIPTION OF DRAWINGS

These and other features of the invention will become more apparent from the following detailed description of a preferred, non-limiting embodiment of it, illustrated by way of example in the accompanying drawings, in which:

FIG. 5 is a front view of the detail of FIG. 4;

FIG. 6 is a sectional view of the detail of FIG. 4 through the plane VI-VI of FIG. 5;

FIG. 7 is a rear view of the detail of FIG. 4;

FIG. 8 is a sectional view of the detail of FIG. 4 through the plane VIII-VIII of FIG. 7;

FIG. 9 is an enlarged perspective view f a second detail of the machine of FIG. 1;

DETAILED DESCRIPTION OF PREFERRED EMBODIMENTS OF THE INVENTION

Figure 1:
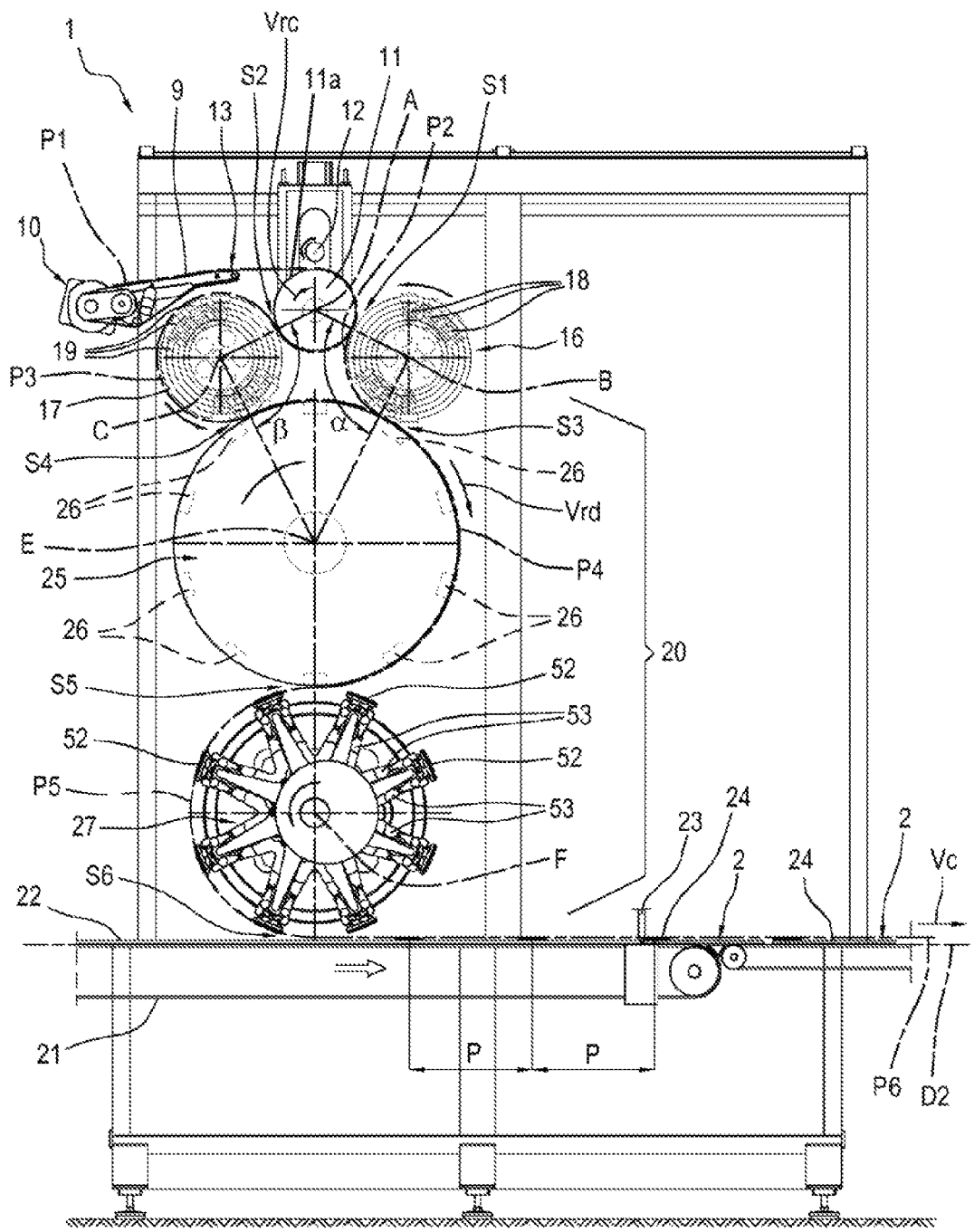
FIG. 1 is a front view of a machine according to this invention.

With reference to FIG. 1, the numeral 1 denotes in its entirety a machine for making absorbent sanitary articles 2 according to this invention.

Figure 2:
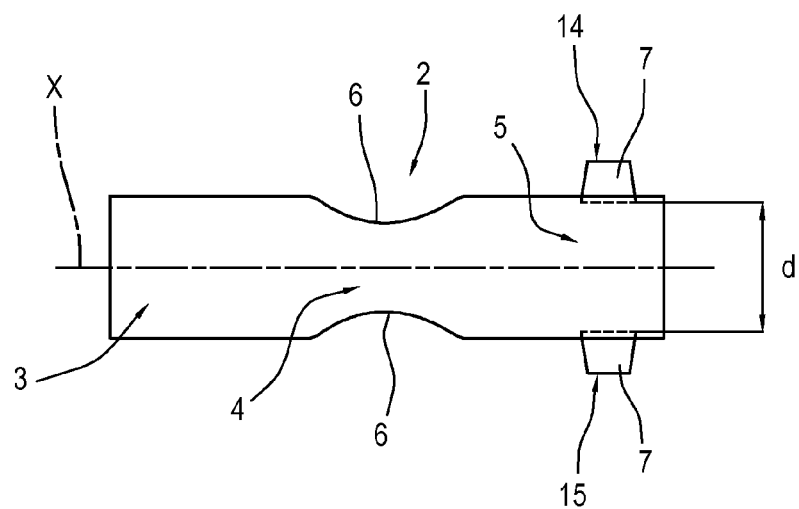
FIG. 2 is a plan view of an absorbent sanitary article obtained from the machine according to this invention.

The absorbent article 2, as shown in detail in FIG. 2, is substantially rectangular in shape and extends along a longitudinal axis X.

The absorbent articles 2 comprise, in a line along the axis X, a front portion 3, a central portion 4 and a rear portion 5.

At the central portion 4, the absorbent articles 2 comprise a recess 6, or leg opening, formed by two arched stretches which are symmetrical relative to the axis X.

The absorbent articles 2 comprise an internal absorbent padding, normally made from cellulose fibres, placed inside a soft container defined on one side by a permeable sheet of non-woven fabric and, on the other side, by an impermeable sheet of polyethylene.

The absorbent article 2 is also equipped with a pair of accessory element, that is lateral flaps 7, extending transversely to the axis X. More specifically, the lateral flaps 7 extend from the rear portion 5 of the absorbent article 2 and are, in use, designed to be placed over respective fastening zones of the front portion 3 in order to close the absorbent article 2 round the wearer's hips.

The lateral flaps 7 generally comprise pieces of a continuous strip 9, defining a longitudinal axis L (FIG. 3a) and preferably made from elastomeric material. Moreover, the lateral flaps 7 have a surface which is partly covered with an adhesive substance, or provided with other quick fastening means.

It should be noted that the accessory elements 7 which, as mentioned above, define the lateral flaps of the absorbent article 2, and are denoted by the same reference numeral 7, therefore also consist of the above-mentioned pieces. In other words, in this specific case, the accessory elements and the lateral flaps coincide and both consist of the above-mentioned pieces.

The machine 1 comprises a device 10 for feeding the above-mentioned continuous strip 9 of elastomeric material to a conveyor roller, labelled 11, and a device 12 for cutting the strip 9 into a continuous and alternating succession 13 of first 14 and second 15 pieces.

The conveyor roller 11 rotates about an axis A parallel to a first reference direction D1, defined by a direction perpendicular to the plane of FIG. 1, and has a relative sucked surface 11a for retaining the above-mentioned succession 13 of first 14 and second 15 pieces during their transfer.

The cutting device 12 preferably comprises a cutting roller, rotating in an anticlockwise direction, which acts in conjunction with the conveyor roller 11, rotating in a clockwise direction about its axis A, in order to make the continuous succession 13 of first 14 and second 15 pieces. More in detail, the first pieces 14 are applied on one side of the article 2 having a first of the above-mentioned recesses 6, whilst the second pieces 15 are applied on the opposite side of the article 2 equipped with the second recess 6.

Figure 3A:
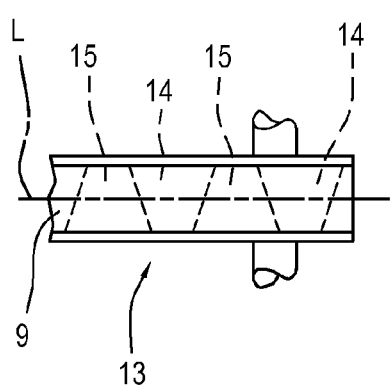
FIGS. 3a, 3b and 3c schematically illustrate several operational steps of the machine.

The cutting roller 12 is equipped, preferably, with a pair of blades which are skew to each other and inclined transversely to the axis of rotation of the roller 12 itself. The blades positioned in this way make cuts which are oblique relative to the longitudinal direction of the continuous succession 13, thus forming substantially trapezoidal pieces 14 and 15 (FIG. 3a).

The machine 1 also comprises a first transfer roller 16, which rotates about a relative axis B parallel to the first direction D1 and it is equipped with a plurality of units 18 for retaining and transferring the first pieces 14, which are picked up by the sucked surface 11a of the conveyor roller 11 at a first pick-up station S1.

The machine 1 also comprises a second transfer roller 17, which rotates about a relative axis C parallel to the first direction D1 and it is equipped with a plurality of units 19 for retaining and transferring the second pieces 15, which are picked up by the sucked surface 11a of the conveyor roller 11 at a second pick-up station S2.

More specifically, it is preferable and advantageous that the first 16 and the second 17 transfer roller are equal, in such a way as to simplify the structure of the machine 1.

As further illustrated in FIG. 1, the machine comprises a unit 20 for forming and applying on a continuous band 22 of absorbent material at least a pair of pieces for each absorbent article 2. Each pair is formed by a first 14 and by a second 15 piece, which are mutually aligned and spaced by a distance d and aligned along the first direction D1.

Downstream of the forming and applying unit 20, the machine 1 comprises a conveyor 21 which is able to feed with a speed vc the continuous band 22 of absorbent material along a second direction D2, at right angles to the above-mentioned direction D1, and a device 23 for cutting the continuous band 22 into pieces 24 of absorbent material designed to constitute single absorbent articles 2.

The forming and applying unit 20 applies the respective pairs of pieces 14 and 15 on the continuous band 22 spaced by a step P, measured along the direction D2. The step P coincides with the step according to which are cut the above-mentioned pieces 24 of absorbent material, designed to constitute the single absorbent articles 2.

The forming and applying unit 20 comprises a spacer roller 25, of known type, which is able to receive, at a third station S3, the first pieces 14 fed by the first transfer roller 16 and is able to receive, at a fourth station S4, the second pieces 15 fed by the second transfer roller 17. The spacer roller 25 is also able to form respective pairs of pieces 14 and 15, wherein the pieces are aligned along the first direction D1 and spaced by an intermediate distance (d').

The spacer roller 25 has a plurality of units 26 and the first 16 and the second 17 transfer roller release to each unit 26, respectively, a first 14 and a second 15 piece, forming in this way one of the pairs of pieces.

The spacer roller 25 then transfers the respective pair of pieces to an accelerator roller 27, of known type, installed downstream.

In detail, each of the units 26 of the spacer roller 25 has, in turn, a first seat and a second seat, not illustrated, for retaining, respectively, the first 14 and the second 15 piece.

During the transfer of the pair of pieces 14 and 15 to the accelerator roller 27, the spacer roller 25 performs, in known manner, a translation of the seats of each unit 26 along respective directions opposite to each other and parallel to the first direction D1, in such a way as to space the pieces 14 and 15 of the pair up to the distance (d) of application on the band 22, before its transfer to the accelerator roller 27.

In other words, from the cutting of the continuous strip 9 of elastomeric material to their application in pairs on the continuous band 22 of absorbent material, the first 14 and the second 15 pieces undergo a first spacing, by the first 16 and the second 17 roller, for being transferred in pairs spaced by the intermediate distance (d'), and subsequently undergo a second spacing, by the spacer roller 25, for being transferred and then applied on the continuous band 22 mutually spaced by the distance (d).

The spacer roller 25 of the pairs of pieces 14 and 15 is substantially tangent to the first 16 and to the second 17 transfer rollers, respectively, at the third S3 and the fourth S4 release stations.

The spacer roller 25 is shown in FIG. 1 rotating about a relative axis E in a clockwise direction, whilst the first 16 and the second 17 transfer rollers are shown rotating in an anticlockwise direction about the respective axes B and C.

The accelerator roller 27 is substantially tangent to the spacer roller 25 at a fifth transfer station S5, wherein the pair of pieces 14 and 15 are transferred. The accelerator roller 27 is shown in FIG. 1 rotating in an anticlockwise direction about a relative axis F, and is also tangent to the above-mentioned conveyor 21 at a sixth station S6 for applying the pairs of pieces 14 and 15.

In detail, the accelerator roller 27 has a plurality of pairs of suction seats 52 designed to retain the pairs of pieces 14 and 15 formed by the spacer roller 25.

Each pair of seats 52 is mounted on a radial shaft 53 which, as the accelerator roller 27 rotates, oscillates about the relative axis F, under the action of actuating cam means (not illustrated).

The spacer roller 25 has a peripheral speed vrd of feeding the relative units 26 and the accelerator roller 27 is able to pick up at the fifth station S5 the pairs of pieces 14 and 15 with a feeding speed of the relative seats 52 equal to the speed vrd.

Moreover, the accelerator roller 27 is able to impart an acceleration to the relative seats 52 and, therefore, to each pair of pieces 14 and 15 picked up by the spacer roller 25, for transferring and coupling the pair of pieces 14 and 15 to the continuous band 22 of absorbent material with a speed equal to the speed vc of feeding the band 22.

Similarly, the above-mentioned conveyor roller 11 transports the continuous and alternating succession 13 of first 14 and second 15 pieces with a feeding speed vrc, and the first 16 and the second 17 transfer rollers, tangent to the conveyor roller 11 at, respectively, the first S1 and the second S2 pick-up stations, are also able to vary the feeding speed of the respective units 18 and 19 for picking up the pieces 14 and 15 with a speed equal to the above-mentioned speed vrc and then release the pieces 14 and 15 to the spacer roller 25 with a speed equal to the above-mentioned speed vrd.

Each of the transfer rollers 16 and 17 comprises a plurality of concentric units 28a, 28b, 28c rotating about a shared axis of rotation, parallel to the first direction D1.

More in detail, according to the preferred embodiment, the roller comprises a first inner unit 28a, a second intermediate unit 28b and a third outer unit 28c.

The axis of rotation of the units 28a, 28b, 28c coincides with the axis B of rotation of the transfer roller 16, and it is defined by a shaft 29 fixed and integral with a frame of the machine 1.

For simplicity of description, the description below refers only to the first transfer roller 16, since, as stated above, it is preferable that the first 16 and the second 17 transfer rollers are equal to each other.

It should be noted that the description for the first roller 16 is to be considered absolutely valid and the same, with regard to the references to components and drawings, for the second roller 17, too.

Figure 4:
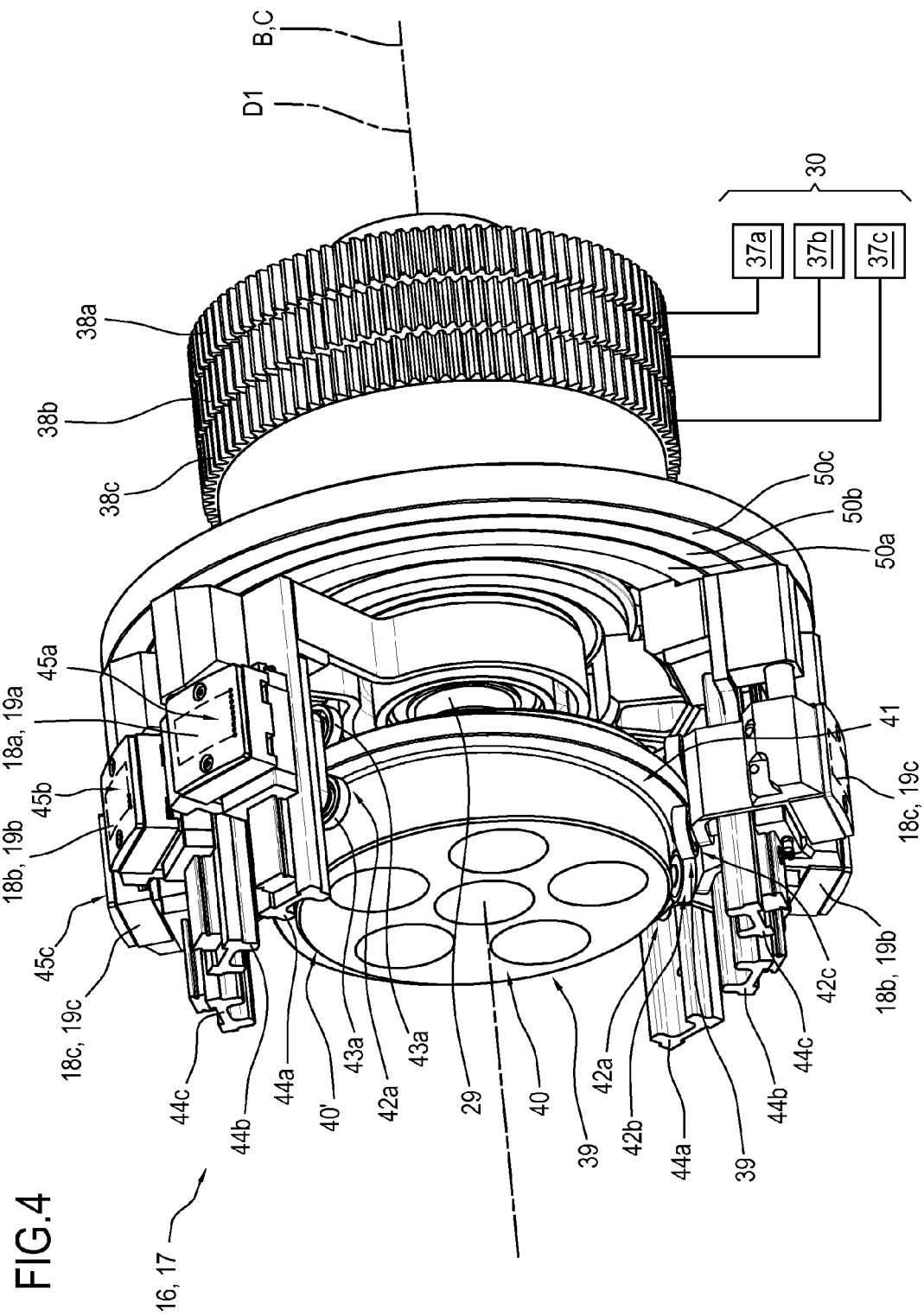
FIG. 4 is a perspective view of a first detail of the machine of FIG. 1.

Looking in more detail, as shown in FIG. 4, each of the units 28a, 28b, 28c carries at least one respective unit 18a, 18b, 18c of the transfer roller 16. In the specific case of the preferred and illustrated embodiment, each unit 28a, 28b, 28c carries a respective pair of units 18a, 18b, 18c, positioned symmetrically opposite each other relative to the axis B of rotation of the unit 28a, 28b, 28c.

The transfer roller 16 comprises motor means, labelled 30 in FIG. 4, which drive each of the units 28a, 28b, 28c and define for each of them a respective law of motion, for picking up the first pieces 14 from the conveyor roller 11 with a first speed, equal to the speed vrc of feeding the continuous and alternating succession 13 drawn by the conveyor roller 11, and for releasing the first pieces 14 to the spacer roller 25 with a second speed, equal to the speed vrd of feeding the units 26 of the spacer roller 25.

More specifically, the units 28a, 28b, 28c are movable, independently of each other and the respective laws of motion defined by the motor means 30 are, therefore, also independent of each other.

For further simplicity of description, the references to identical and corresponding components for each unit will be indicated with the same numbering and those associated with the first inner unit 28a will be indicated with "a", those associated with the second intermediate unit 28b will be indicated with "b" and those associated with the third outer unit 28c will be indicated with "c".

As shown more clearly in FIG. 6, the units 28a, 28b, 28c are able to move independently of each other thanks to respective pairs 31a, 31b, 31c of concentric bearings with gradually increasing dimensions.

More in detail, a first pair 31a of bearings is fitted on the fixed shaft 29 and carries the first unit 28a. A second pair 31b of bearings, with a diameter greater than the first pair, is fitted on the first unit 28a and carries the second unit 28b. Lastly, a third pair 31c of bearings, with a diameter greater than the first pair and the second pair, is fitted on the second unit 28b and carries the third unit 28c.

Each unit 28a, 28b, 28c comprises a respective main body 32a, 32b, 32c, which is substantially tubular in shape. Each main body 32a, 32b, 32c has, respectively, a relative inner surface 33a, 33b, 33c and a relative outer surface 34a, 34b, 34c.

The first pair 31a of bearings is, therefore, mounted between the shaft 29 and the inner surface 33a of the first unit 28a; the second pair 31b is mounted between the outer surface 34a of the first unit 28a and the inner surface 33b of the second unit 28b; the third pair 31c is mounted between the outer surface 34b of the second unit 28b and the inner surface 33c of the third unit 28c.

Moreover, each unit 28a, 28b, 28c has, respectively, a front portion 35a, 35b, 35c and a rear portion 36a, 36b, 36c.

At the rear portion 35a, 35b, 35c each unit 28a, 28b, 28c is connected, separately from the others, to the above-mentioned motor means 30.

In detail, the motor means 30 comprise a plurality of motor units, schematically represented by the blocks 37a, 37b, 37c (FIG. 4). The motor units 37a, 37b, 37c are separate and distinct from each other and each of them is connected to a respective unit 28a, 28b, 28c. More in detail, a first motor unit 37a is connected to the first unit 28a, a second motor unit 37b is connected to the second unit 28b and a third motor unit 37c is connected to the third unit 28c.

Each of the motor units 37a, 37b, 37c is able to define the law of motion for the unit to which it is connected comprising a non-circular gear wheel gearing (not illustrated), or by using three different electronic cams (also not illustrated) consisting of three different motors, each coupled to the respective motor unit.

Each of the gearings is connected to the respective unit 28a, 28b, 28c by means of a plurality of gear wheels 38a, 38b, 38c integral with the units 28a, 28b, 28c at the rear portion 35a, 35b, 35c of the units (FIGS. 4 and 6).

According to the preferred embodiment, the transfer roller 16 has a first 38a, a second 38b and a third 38c gear wheel, integral, respectively, with the first 28a, the second 28b and the third 28c unit.

The gear wheels 38a, 38b, 38c also have equal diameters and are substantially adjacent to each other along the axis B of rotation of the roller 16.

The first transfer roller 16 comprises means 39 for translating the relative units 18a, 18b, 18c along a first direction T1 parallel to the first direction D1 (FIGS. 10 and 11), between a position for picking up the first pieces 14 from the conveyor roller 11, at the first station S1, and a position for releasing the pieces 14 to the spacer roller 25, at the third station S3.

As shown in FIG. 4, the means 39 for translating the units 18*a*, 18*b*, 18*c* comprise a fixed cam 40 having a relative profile 41, the cam 40 being integral with the above-mentioned shaft 29 of the roller 16. The translational means 39 also comprise a plurality of carriages 42*a*, 42*b*, 42*c*, slidably coupled with the profile 41 of the cam 40, each of which is mounted on a respective unit 18*a*, 18*b*, 18*c* of the roller 16.

More in detail, in the example illustrated, the cam 40 is of the cylindrical type and the profile 41 is defined by a projection made on a cylindrical lateral surface 40' of the cam 40.

Each carriage 42*a*, 42*b*, 42*c* comprises a pair of rollers 43*a*, 43*b*, 43*c* slidably coupled on respective opposite surfaces, labelled 41' and 41", of the profile 41 of the cam 40.

The transfer roller 16 comprises, for each relative unit 18*a*, 18*b*, 18*c*, a guide 44*a*, 44*b*, 44*c*, connected to the respective unit 28*a*, 28*b*, 28*c* and integral with it in rotation. Each guide 44*e*, 44*b*, 44*c* has a main direction of extension along a direction parallel to the first reference direction D1.

During the rotation of the units 28*a*, 28*b*, 28*c* about the axis B of rotation, each carriage 42*a*, 42*b*, 42*c* follows the profile 41 of the cam 40 and, consequently, the unit 18*a*, 18*b*, 18*c* translates on the respective guide 44*a*, 44*b*, 44*c* between the pick up position (FIG. 10) of the first pieces 14 from the conveyor roller 11, wherein the respective unit 18*a*, 18*b*, 18*c* is in a position close to the relative unit 28*a*, 28*b*, 28*c*, and the release position (FIG. 11) of the pieces 14 to the spacer roller 25, wherein the unit 18*a*, 18*b*, 18*c* is in a position far from the relative unit 28*a*, 28*b*, 28*c*.

During the movement from the pick up position to the release position, each unit 18*a*, 18*b*, 18*c* translates, along the above-mentioned direction T1, the respective first piece 14 picked up from the continuous succession 13, by a distance equal to half the above-mentioned intermediate distance.

Figure 10:
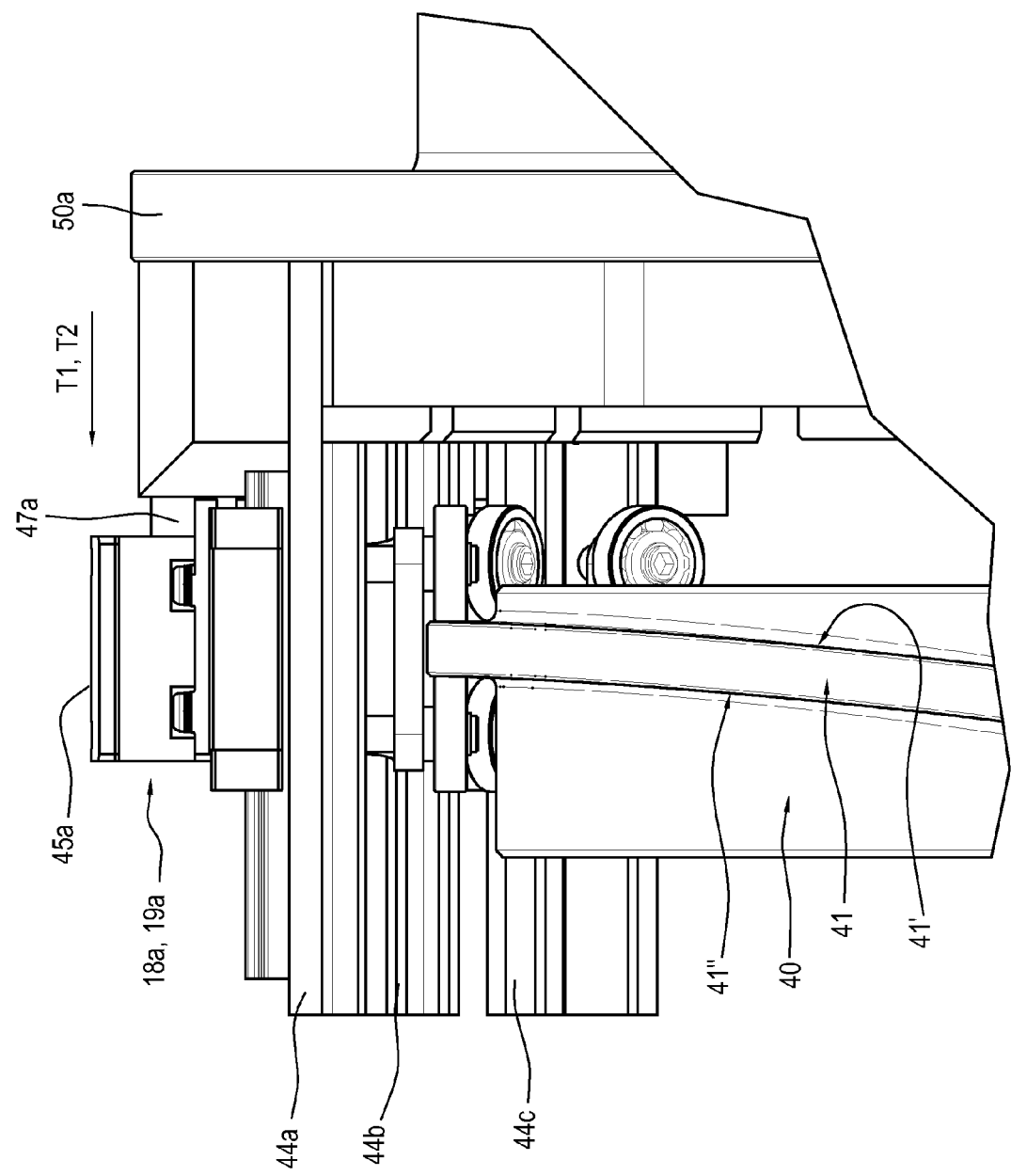
FIGS. 10 and 11 are enlarged side views of the second detail of FIG. 9, according to respective operating configurations.
Figure 11:
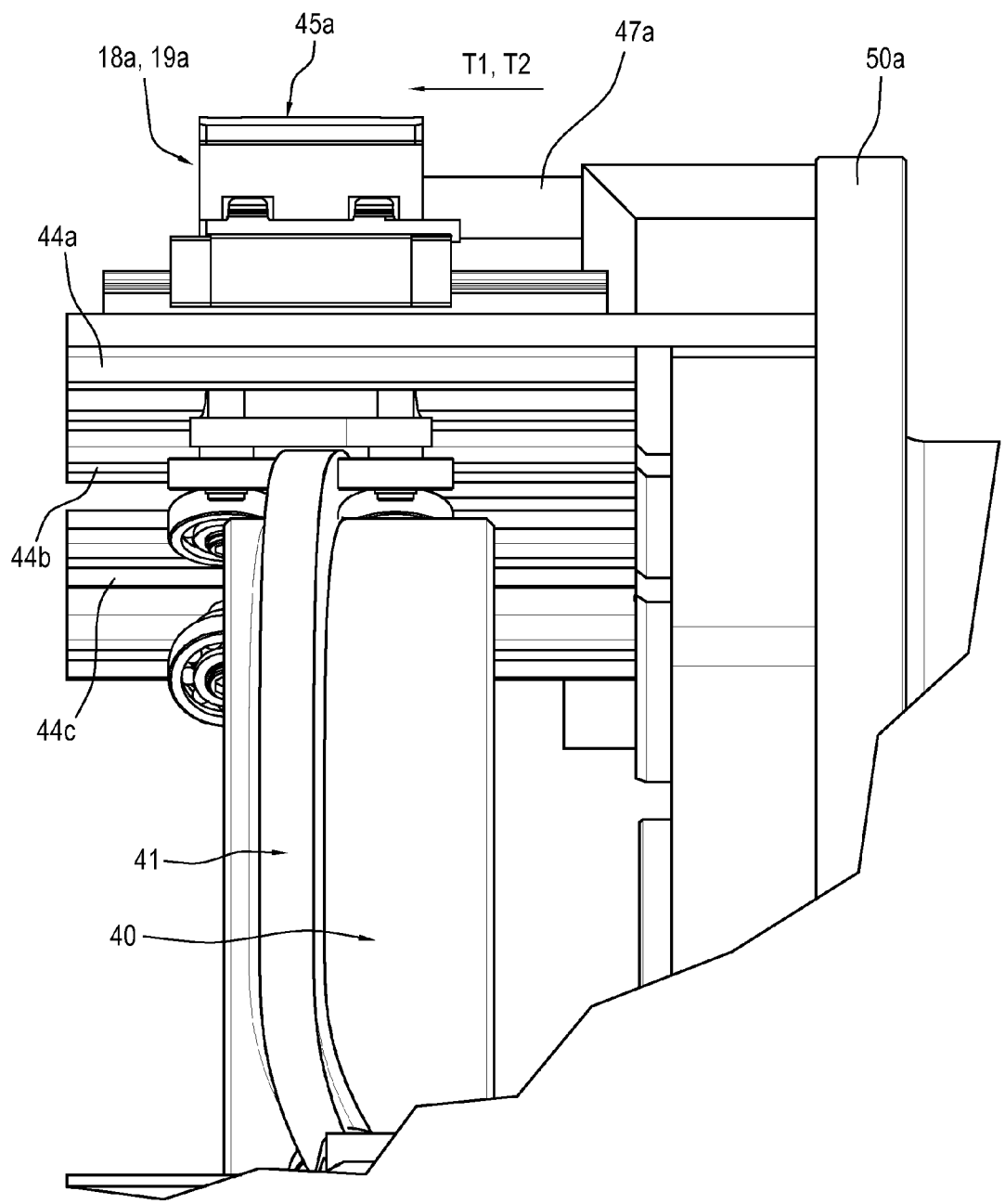

Similarly, the second transfer roller 17 translates the second pieces 15 by a distance equal to half the intermediate distance, along a second direction T2 parallel to the direction D1 and opposite in direction to the direction T1 (FIGS. 10 and 11).

In this way, when the first 14 and the second 15 pieces are released to the spacer roller 25 to form the above-mentioned pairs, the distance between them is equal to the distance d'.

Each unit 18*a*, 18*b*, 18*c* has a respective suction face 45*a*, 45*b*, 45*c* for retaining the piece 14. The suction is obtained using the holes 46*a*, 46*b*, 46*c* each respective face 45*a*, 45*b*, 45*c* is equipped with (FIG. 9).

The holes 46*a*, 46*b*, 46*c* of each face 45*a*, 45*b*, 45*c* are connected to a respective hollow rod 47*a*, 47*b*, 47*c*, which in turn is in fluid communication with a suction source, indicated schematically by the block 48.

Label 47*a* in FIG. 8 denotes the stem of the unit 18*a* connected to the first inner unit 28*a*. The stem 47*a* is slidable inside a seat 49*a* also connected to the suction source 48. Moreover, the seat 49*a* has a length such that the stem 47*a* always remains engaged with the seat 49*a* during the sliding of the unit 18*a*, even in the condition of maximum excursion of the unit 18*a*, at the release position of the piece 14.

This guarantees that the piece 14 remains correctly gripped until the moment of its release to the spacer roller 25.

Obviously, what has just been described is to be considered similarly valid for the units 18*b* and 18*c*.

The first transfer roller 16 also comprises a plurality of concentric elements 50*a*, 50*b*, 50*c*, each of which is connected to a respective unit 18*a*, 18*b*, 18*c* and is integral with it in rotation. More in detail, the elements 50*a*, 50*b*, 50*c* are substantially annular in shape.

The annular elements 50*a*, 50*b*, 50*c* constitute valve elements for the respective units 18*a*, 18*b*, 18*c*, since they define, during the rotation of the units 18*a*, 18*b*, 18*c* about the axis B of rotation, a first operating condition, wherein the suction holes 46*a*, 46*b*, 46*c* are placed in fluid communication with the suction source 48 for retaining the first pieces 14, and a second operating condition, wherein the fluid communication between the holes 46*a*, 46*b*, 46*c* and the suction source 48 is interrupted for releasing the pieces 14.

As shown in FIGS. 5 and 6, the first roller 16 comprises a first 50*a*, a second 50*b* and a third 50*c* annular element connected, respectively, to the first 18*a*, the second 18*b* and the third 18*c* unit.

Preferably, the annular elements 50*a*, 50*b*, 50*c* are made from self-lubricating material, for example Teflon, in such a way as to prevent the formation of friction, between two adjacent elements, during the rotation of the units 18*a*, 18*b*, 18*c*.

The fluid communication between the holes 46*a*, 46*b*, 46*c* and the suction source 48 is achieved, for each unit 18*a*, 18*b*, 18*c*, by means of a respective through hole 51*a*, 51*b*, 51*c* (FIGS. 7 and 8), made on the respective annular element 50*a*, 50*b*, 50*c*, the hole 51*a*, 51*b*, 51*c* placing in communication the source 48 with the respective seat 49*a*, 49*b*, 49*c* of each unit 18*a*, 18*b*, 18*c*.

Since, according to the preferred embodiment, each unit 28*a*, 28*b*, 28*c* carries a pair of units 18*a*, 18*b*, 18*c* diametrically opposite the axis B of rotation of the first roller 16, each annular element 50*a*, 50*b*, 50*c* has a pair of holes 51*a*, 51*b*, 51*c*, also diametrically opposite the axis B, each of which places the source 48 in fluid communication with a respective unit 18*a*, 18*b*, 18*c* of the pair.

Since each annular element 50*a*, 50*b*, 50*c* is integral with the respective unit 18*a*, 18*b*, 18*c*, the above-mentioned hole 51*a*, 51*b*, 51*c* always places in communication each seat 49*a*, 49*b*, 49*c* of the units 18*a*, 18*b*, 18*c* and the respective suction holes 46*a*, 46*b*, 46*c* with the suction source 48.

The first roller 14 is equipped with a further element, not illustrated, which also acts as a valve and it is interposed between the annular elements 50*a*, 50*b*, 50*c* and the suction source 48 and allows definition of the fluid connection steps with the suction source 48 and interruption of the connection.

Looking in more detail at the operation of the machine 1, it receives the continuous band 22 of absorbent material, which is transported by the conveyor 21 along the second direction D2.

The machine 1 also receives the strip 9 of elastomeric material which is fed from the feeding device 10 to the conveyor roller 11.

The strip 9 is cut at the conveyor roller 11, by the cutting roller 23, into the above-mentioned continuous and alternating succession 13 of first 14 and second 15 pieces, constituting, as already stated, the first and second flaps of the absorbent article 2.

The continuous strip 9 and the succession 13 of pieces 14 and 15 are moved by the feeding device 10 and by the conveyor roller 11 following a first stretch P1 of the overall path of the pieces 14 and 15 from the cutting of the strip 9 to their application on the band 22 made of absorbent material.

At the first station S1 the first transfer roller 16 picks up from the conveyor roller 11 the first pieces 14 and feeds them to the spacer roller 25 following a second stretch P2 of path.

The second roller 17 picks up, at the second station S2, the second pieces 15 and feeds them to the spacer roller 25 following a third stretch P3 of path, different from the second stretch P2.

The first 16 and the second 17 rollers pick up the respective pieces 14 and 15 varying the feeding speed of the relative respective units 18 and 19 until it is changed to the value of the above-mentioned peripheral speed vrc of the conveyor roller 11.

After picking up the respective pieces 14 and 15, each roller 16 and 17 holds the relative pieces 14 and 15, varying again the speed of the relative units 18 and 19 to change it to the value of the speed vrd of the units 26 of the spacer roller 25.

The transfer rollers 16 and 17 then translate the relative pieces 14 and 15 transported along the respective directions T1 and T2 parallel to the first direction D1 and, since these directions T1 and T2 have directions opposite to each other, the spacer roller 25 receives an above-mentioned pair of first 14 and second 15 pieces, which are mutually aligned and spaced along the first reference direction D1 by the intermediate distance (d').

As stated above, the first 16 and the second 17 transfer rollers rotate in an anticlockwise direction, whilst the spacer roller 25 rotates in a clockwise direction, so, the second roller 17 releases firstly the relative second piece 15, at the fourth station S4, then the first roller 16 releases the relative first piece 14 at the third station S3.

Therefore, the spacer roller 25 forms the respective pairs of pieces 14 and 15 at the third station S3, when it receives the first piece 14.

At the third station S3 there is the joining of the second P2 and the third P3 stretch into a single fourth stretch, labelled P4 in FIG. 1, which each pair of pieces 14 and 15 travels along from the third station S3 to the fifth station S5, in the direction of the accelerator roller 27.

The spacer roller 25 then transfers the pair of pieces 14 and 15 to the accelerator roller 27 following the fourth stretch P4 of shared path.

During the feeding along the fourth stretch P4, the spacer roller 25 forms the further mutual spacing of the pieces 14 and 15 of each pair, until moving them to a distance equal to the distance (d) of application of the pair on the continuous band 22 of absorbent material.

Figure 3B:
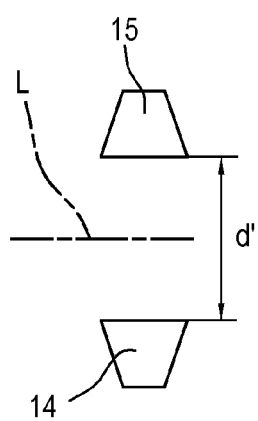
Figure 3C:
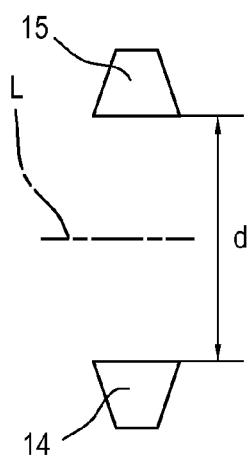

FIGS. 3a, 3b and 3c schematically indicate the sequence of steps performed by the machine 1 for making the pairs of pieces 14 and 15, or lateral flaps, to be applied to the continuous band 22.

Initially, transversal notches are made on the continuous strip 9 of elastomeric material to define the continuous and alternating succession 13 of first 14 and second 15 pieces (FIG. 3a). This step is implemented by notching, using the cutting roller 23, the strip 9 with respective slanting notches which define first 14 and second 15 trapezoidal pieces.

The first 14 and the second 15 pieces are then picked up, respectively, by the first 16 and the second 17 transfer rollers and translated along the respective directions T1 and T2, until they are spaced by the intermediate distance (d') (FIG. 3b).

More in detail, as stated, the pieces 14 and 15 are substantially trapezoidal in shape and the first 16 and the second 17 transfer rollers translate the respective pieces along the directions T1 and T2, mutually away from the longitudinal axis L of the strip 9, keeping the longer side facing towards the axis L and moving them both to a distance from the axis L equal to half the above-mentioned intermediate distance d'.

Lastly, the spacer roller 25 performs the further spacing of the pieces 14 and 15 of the pair, carrying them to a mutual distance equal to the distance d of transfer to the accelerator roller 27 and application on the band 22 (FIG. 3c).

At the fifth station S5, the accelerator roller 27 picks up the pairs of pieces 14, 15 with a speed of feeding the relative suction seats 52 equal to the value of speed vrd of the units 26 of the spacer roller 25 and transfers the pairs of pieces 14 and 15 following a fifth stretch P5 of path, increasing their feeding speed for applying them on the band 22 of absorbent material with a speed equal to the speed vc of feeding the band 22.

When the pairs of pieces 14 and 15 have then been applied to the band 22 of absorbent material the absorbent articles 2 joined together move forward towards the cutting unit 23 and the outfeed of the machine, following with speed vc a sixth stretch S6 of path, substantially defined by the conveyor 21.

With regard to the operation of each transfer roller, a more detailed description of the movement and the mutual coordination of the relative components is given below, with particular reference to the movement and coordination of the units 18 carried by each unit 28a, 28b, 28c.

In order to make the description of the units 18 of each pair associated with the respective unit 28a, 28b, 28c of the roller 16 clearer, 18a' and 18a' will indicate the units of the first pair carried by the first unit 28a, 18b' and 18b" will indicate the units of the pair carried by the second unit 28b and 18c' and 18c" will indicate the units of the pair carried by the third unit 28c, respectively.

During the rotation about the axis B, the speed of feeding the unit 18a' of the first unit 28a is changed to the value of the peripheral speed vrc of the conveyor roller 11, for picking up the first piece 14 at the first station S1.

It is preferable that the unit 18a' reaches that speed before arriving at the first station S1 and it is also preferable that it maintains it for a predetermined stretch downstream of the first station S1, so as to guarantee the correct pick up of the piece 14.

After the pick up, the speed of the unit 18a' is changed to the value of the peripheral speed vrd of the spacer roller 25.

More specifically, according to the preferred embodiment, the spacer roller 25 has a peripheral speed vrd greater than the peripheral speed vrc of the conveyor roller 11, so, after picking up the first piece 14, the unit 18a' is accelerated when moving from the first S1 to the third S3 station.

It is also preferable that the unit 18a' reaches the speed vrd before arriving at the third station S3 and that it maintains it for a predetermined stretch downstream of the station, so as to guarantee the correct release of the first piece 14 to the spacer roller 25.

After releasing the first piece 14, in reaching again the first station S1, the unit 18a' is slowed down and its speed is returned to the value of the peripheral speed vrc for picking up a new first piece 14 from the conveyor roller 11.

As already indicated, each unit 28a, 28b, 28c carries a pair of units 18a' and 18a", the one diametrically opposite the other relative to the axis B of rotation.

For this reason, each unit 18a' and 18a" is given the same acceleration and the same deceleration given to the other.

In other words, when the speed of the unit 18a' is slowed down to the speed vrc for picking up from the conveyor roller 11 the first piece 14, the unit 18a" undergoes the same slowing down.

More in detail, during the step for picking up the first piece 14 by the unit 18a', the unit 18a" is empty as it has just released the relative first piece 14 to the spacer roller 25 and is therefore moving from the third S3 to the first S1 station.

When, then, the unit 18a', carrying the first piece 14, is accelerated to change its feeding speed to the peripheral speed vrd of the spacer roller 25, the unit 18a" simultaneously accelerates.

When the unit 18a" then approaches the first station S1, it is slowed down to the speed vrc, and at the same time the unit 18a', which has just transferred to the spacer roller 25 the relative first piece 14, is also changed to the speed vrc.

The unit 18a", which has picked up from the conveyor roller 11 a first piece 14, is now accelerated until reaching the speed vrd and simultaneously the unit 18a' is also accelerated.

Lastly, after the unit 18a" has released the piece 14 to the spacer roller 11, the unit 18a' is slowed down to pick up a new piece 14 from the conveyor roller 11 and restart the cycle.

Obviously, according to the above description, the unit 18a" also reaches the speeds vrc and vrd before reaching the first S1 and the third S3 station, and they are maintained for a predetermined stretch downstream of the stations, so as to guarantee the correct pick up and the correct release of the first piece 14 also by the unit 18a".

To have the correct coordination of the steps for picking up and releasing the first piece 14 by the unit 18a' and the unit 18a" according to the above-mentioned predetermined speeds, it is preferable that the first S1 and the third S3 stations are positioned, along the path travelled by the units during their rotation about the axis B, spaced from each other by an arc-shaped stretch of the above-mentioned path having a subtended angle, labelled α in FIG. 1, substantially equal to 90°.

The spacing between the first S1 and the third S3 stations allows maximum continuity between the steps for picking up and releasing the first pieces 14 without interferences between the movements of the various units 18a, 18b, 18c during the respective accelerations and decelerations.

Further, with regard to the units 18b', 18b" and 18c', 18c" carried by the other units 28b and 28c, they are given the same accelerations and the same decelerations as the units 18a', 18a" carried by the first unit 28a described above.

Further, the conveyor roller 11 and the spacer roller 25 rotate with constant rotational speed, so, to have continuous pick up and release of the pieces 14 by the first transfer roller 16, it is preferable that each unit 18a', 18a", 18b', 18b", 18c', 18c" of the respective unit 28a, 28b, 28c is accelerated and decelerated at the same positions whilst reaching the first S1 and the third S3 station.

In this way, the laws of motion with which each unit 28a, 28b, 28c of the first roller 16 is moved are equal to each other. Moreover, as the first transfer roller 16 is equipped, according to the preferred embodiment, with three concentric units, the phase displacement between one law of motion and the other is equal to a third of a revolution.

It should be noted once again that the considerations just made for the first transfer roller 16 are to be considered absolutely valid for the second transfer roller 17, too.

More specifically, also for the second roller 17 it is preferable that the second S2 and the fourth S4 stations are positioned, along the circular path travelled by the relative units 19 during the rotation about the axis C, spaced from each other by an arc-shaped stretch of the above-mentioned path, having a subtended angle, labelled β in FIG. 1 substantially equal to 90°, thereby avoiding, also for the second roller 17, possible interferences between the movements of the units 19.

In order to obtain the above-mentioned values of the angle α and of the angle β, the diameters of the transfer rollers 16 and 17, of the conveyor roller 11 and of the spacer roller 25 are suitably dimensioned.

More in detail, according to the preferred embodiment, the transfer rollers 16 and 17 have a diameter substantially equal to 450 mm; the conveyor roller 11 has a diameter of between 150 and 155 mm; the spacer roller 25 has a diameter of between 645 and 650 mm.

Moreover, the laws of motion with which the units 28a, 28b, 28c of the second roller 17 are driven are also synchronised with each other to obtain the continuity in the picking up and releasing of the second pieces 15, as described for the laws of motion of the units 28a, 28b, 28c of the first roller 16. More specifically, similarly to the roller 16, the laws of motion of the second roller 17 are equal but offset by a third of a revolution from each other.

The invention described above is susceptible of industrial application and may be modified and adapted in several ways without thereby departing from the scope of the inventive concept. Moreover, all the details of the invention may be substituted for technically equivalent elements.

The invention claimed is:

1. A machine for making absorbent sanitary articles, comprising
   a feeding device for feeding a continuous strip to a conveyor roller, rotating about an axis parallel to a first direction,
   a strip cutting device for cutting the strip in a continuous and alternating succession of first and second pieces, comprising, respectively, first and second accessory elements of the absorbent article,
   a forming and applying unit for forming and applying on a continuous band of absorbent material, fed by a conveyor along a second direction at a right angle to the first direction, at least a pair of accessory elements for each absorbent article, comprising the first piece and the second piece aligned and spaced at an end distance along the first direction;
   a band cutting device for cutting the continuous band into pieces of absorbent material designed to constitute single absorbent articles, following application of the accessory elements,
   a first transfer roller and a second transfer roller rotating about respective axes parallel to the first direction, each of the first and second transfer rollers including a plurality of picking units for picking up, respectively, the first and the second pieces, from the succession and their release on the forming and applying unit
   wherein each of the first and second transfer rollers comprises:
   a plurality of concentric units rotating independently of each other about a shared axis of rotation, each of the concentric units carrying at least one of the plurality of picking units,
   a motor drive system for defining a respective motion sequence for each of the concentric units, and
   a translating system for translating the picking units along a direction parallel to the first direction, between a position for picking up the pieces, at the conveyor roller, and a position for releasing the pieces, at the forming and applying unit.

2. The machine according to claim 1, wherein the motor drive system comprises a plurality of motor units which are separate and distinct from each other, each of the motor units being connected to a respective concentric unit.

3. The machine according to claim 1, wherein each of the motor units comprises a non-circular gear wheel gearing, which defines the respective motion sequence for the respective concentric unit.

4. The machine according to claim 1, wherein the respective motion sequence defines a variation in the speed of rotation of the respective concentric unit, for picking up the pieces from the conveyor roller with a first speed and releasing them on the forming and applying unit with a second speed.

5. The machine according to claim 1, wherein the translating system comprises a fixed cam, integral with a fixed shaft and having a respective profile, and a plurality of carriages, slidably coupled with the profile of the fixed cam, each of the carriages being mounted on a respective picking unit of a respective one of the first and second transfer rollers.

6. The machine according to claim 1, wherein each of the first and second transfer rollers comprises, for each respective picking unit, a guide connected to the respective concentric unit and integral with the respective concentric unit in rotation, and the respective picking unit being slidable on the guide during translating of the respective picking unit.

7. The machine according to claim 1, wherein directions of translation of the first and second pieces are opposite to each other, so as to transfer to the forming and applying unit respective pairs of first and second pieces, mutually aligned and spaced, along the first direction, by an intermediate distance.

8. The machine according to claim 1, wherein each of the first and second transfer rollers comprises a plurality of concentric elements, each of which being connected to a respective picking unit, and integral with the respective picking unit in rotation; each respective picking unit having a face equipped with suction holes and the concentric elements constituting valve elements for the respective picking units and defining, during the rotation of the respective picking units about the axis of rotation of the respective one of the first and second transfer rollers, a first condition, wherein the holes are placed in fluid communication with a suction source for retaining the pieces, and a second condition, wherein the fluid communication between the holes and the suction source is interrupted for releasing the pieces.

9. The machine according to claim 8, wherein the concentric elements are made from a self-lubricating material.

10. The machine according to claim 1, wherein the forming and applying unit comprises:
a spacer roller which receives the first piece, at a first station, and the second piece, at a second station, and forms respective pairs of accessory elements, comprising a first and a second piece aligned along the first direction and spaced by an intermediate distance;
the spacer roller having a plurality of retaining and transferring units for retaining and transferring each pair to an accelerator roller;
the retaining and transferring units of the spacer roller translating each piece of the pair, along respective directions opposite to each other and parallel to the first direction, for spacing the pieces up to the end distance of applying the pair on the continuous band of absorbent material, before transferring the pair to the accelerator roller;
the accelerator roller imparting an acceleration to each pair fed by the spacer roller for transferring and coupling the pair to the continuous band of absorbent material with a speed equal to a speed of feeding the band, set by the conveyor.

11. The machine according to claim 2, wherein each of the motor units comprises a respective electronic cam formed by a corresponding independent electric motor, which defines the motion sequence for the respective concentric unit.

12. The machine according to claim 3, wherein each of the motor units comprises a respective electronic cam formed by a corresponding independent electric motor, which defines the motion sequence for the respective concentric unit.

13. The machine according to claim 5, wherein the motor drive system comprises a plurality of motor units which are separate and distinct from each other, each of the motor units being connected to a respective concentric unit.

14. The machine according to claim 13, wherein each of the motor units comprises a non-circular gear wheel gearing, which defines the respective motion sequence for the respective concentric unit.

15. The machine according to claim 14, wherein each of the motor units comprises a respective electronic cam formed by a corresponding independent electric motor, which defines the motion sequence for the respective concentric unit.

16. The machine according to claim 7, wherein the forming and applying unit comprises:
a spacer roller which receives the first piece, at a first station, and the second piece, at a second station, and forms respective pairs of accessory elements, comprising a first and a second piece aligned along the first direction and spaced by the intermediate distance;
the spacer roller having a plurality of retaining and transferring units for retaining and transferring each pair to an accelerator roller;
the retaining and transferring units of the spacer roller translating each piece of the pair, along respective directions opposite to each other and parallel to the first direction, for spacing the pieces up to the end distance of applying the pair on the continuous band of absorbent material, before transferring the pair to the accelerator roller;
the accelerator roller imparting an acceleration to each pair fed by the spacer roller for transferring and coupling the pair to the continuous band of absorbent material with a speed equal to a speed of feeding the band, set by the conveyor.

* * * * *